United States Patent
Wong

(10) Patent No.: US 6,794,412 B1
(45) Date of Patent: Sep. 21, 2004

(54) TREATMENT OF THROMBOSIS BY COMBINED USE OF A FACTOR XA INHIBITOR AND ASPIRIN

(75) Inventor: Pancras C. Wong, Wilmington, DE (US)

(73) Assignee: Bristol-Myers Squibb Pharma Company, Princeton, NJ (US)

(*) Notice: Subject to any disclaimer, the term of this patent is extended or adjusted under 35 U.S.C. 154(b) by 0 days.

(21) Appl. No.: 09/519,188

(22) Filed: Mar. 6, 2000

Related U.S. Application Data

(60) Provisional application No. 60/123,815, filed on Mar. 11, 1999.

(51) Int. Cl.[7] .................. A61K 31/19; A61K 31/47; A61K 31/44
(52) U.S. Cl. .................. 514/570; 514/309; 514/355
(58) Field of Search ................ 514/570, 309, 514/355, 56

(56) References Cited

U.S. PATENT DOCUMENTS

| | | | | |
|---|---|---|---|---|
| 5,308,755 A | * | 5/1994 | Nesheim et al. | 435/7.4 |
| 5,571,784 A | * | 11/1996 | Reers et al. | 514/2 |
| 5,612,353 A | * | 3/1997 | Ewing et al. | 514/309 |
| 5,886,191 A | * | 3/1999 | Dominguez et al. | 598/491 |
| 6,020,331 A | * | 2/2000 | Kahn | 514/221 |
| 6,060,491 A | * | 5/2000 | Pruitt et al. | 514/355 |
| 6,117,896 A | * | 9/2000 | Qabar et al. | 514/384 |
| 6,130,231 A | * | 10/2000 | Wityak et al. | 514/312 |
| 6,136,794 A | * | 10/2000 | Cook et al. | 514/56 |
| 6,140,504 A | * | 10/2000 | Klein et al. | 546/330 |

FOREIGN PATENT DOCUMENTS

| | | |
|---|---|---|
| CA | 2199642 | * 9/1998 |
| DE | 19816983 | 10/1999 |
| EP | 0735050 | 10/1996 |
| EP | 0832879 | 4/1998 |
| WO | WO9412204 | 6/1994 |
| WO | 9514683 | 1/1995 |
| WO | WO9640744 | 12/1996 |
| WO | 9828269 | 2/1998 |
| WO | WO9938827 | 8/1999 |
| WO | WO9945913 | 9/1999 |

OTHER PUBLICATIONS

Harke et al., Antithrombotic Strategies Targeting Thrombin Activities, Thrombin Receptor and Thrombin Generation, *Thrombosis and Haemostasis,* 1997, pp. 736–741.

Kaiser, B., Thrombin and Factor Xa Inhibitors, *Drugs of the Future,* 1998, pp.423–436.

Hara et al., DX–9065a, a New Synthetic, Potent Anticoagulant and Selective Inhibitor for Factor Xa, *Thrombosis and Haemostasis,* 1994, pp.314–319.

Yamazaki et al., Effect of DX–9065a, an Orally Active, Newly Synthesized and Specific Inhibitor of Factor Xa, Against Experimental Disseminated Intravascular Coagulation in Rats, *Thrombosis and Haemostasis,* 1994, pp. 393–396.

Kawasaki et al., Effect of a Synthetic Factor Xa Inhibitor, YM–60828, on Blood Vessel Patency in Combination with a Thrombolytic Agent and on Blood Loss from the Operation Site in a Rat Model or Arterial Thrombosis, *Thrombosis and Haemostasis.*

Lefkovits, Jeffrey et al.: "Selective inhibition of factor Xa is more efficient than factor VIIa–tissue factor complex blockade at facilitating coronary thrombolysis in the canine model" J. Am. Coll. Cardiol. (1996), 28(7), 1858–1865.

* cited by examiner

*Primary Examiner*—Vickie Kim

(57) ABSTRACT

Provided is a method of treating thrombosis in mammals by administering therapeutically effective amounts of a combination of (i) a Factor Xa inhibitor, and (ii) a compound selected from the group consisting of aspirin, TPA, a GPIIb/IIIa antagonist, low molecular weight heparin and heparin, wherein the dose administered for at least one of (i) and (ii) is a subtherapeutic dose. Preferably, the combination of (i) and (ii) provides a synergistic effect.

4 Claims, 5 Drawing Sheets

TREATMENT OF THROMBOSIS BY COMBINED USE OF A FACTOR XA INHIBITOR AND ASPIRIN

CROSS-REFERENCE TO RELATED APPLICATIONS

This application claims the priority benefit of U.S. Provisional Application No. 60/123,815, filed Mar. 11, 1999, which is expressly incorporated fully herein by reference.

FIELD OF THE INVENTION

This invention relates to the treatment of thrombosis in mammals and more particularly to such treatment by the administration of a combination of (i) a Factor Xa inhibitor, and (II) a compound selected from the group consisting of aspirin, TPA, GPIIb/IIIa antagonist, low molecular weight heparin and heparin, wherein the dose administered for at least one of (i) and (ii) is a subtherapeutic dose.

BACKGROUND OF THE INVENTION

The selected class of Factor Xa inhibitors and the selected class of aspirin, GPIIb/IIIa antagonist, tissue plasminogen activator (TPA), low-molecular-weight-heparin and heparin are essential as component parts of the novel compositions of this invention. Aspirin and GPIIb/IIIa antagonists are known in the art as antiplatelet agents. Tissue plasminogen activator (TPA) is known as a thrombolytic agent. Low-molecular-weight heparin and heparin are known as anticoagulants.

Factor Xa is a blood coagulation protein. It plays a major role in blood coagulation because of its central position at the convergent point of the intrinsic and extrinsic pathways of coagulation. It is believed that inhibition of Factor Xa may eliminate the production of thrombin by either the extrinsic or intrinsic pathways without interfering with a basal level of thrombin activity necessary for normal hemostasis (Harke L A, Hanson S R and Kelly A B. Antithrombotic strategies targeting thrombin activities, thrombin receptors and thrombin generation. Thrombosis and Haemostasis 78: 736–741, 1997).

Both peptide and nonpeptide Factor Xa inhibitors are currently available (Kaiser B. Thrombin and factor Xa inhibitors. Drugs of the Future 23: 423–436, 1998). Examples of peptide Factor Xa inhibitors are antistasin and tick anticoagulant peptide, and nonpeptide Factor Xa inhibitors are described in WO98/2326, Thromb Haemost 1994; 71: 314–9, Thromb Haemost 1994; 72:393–6, and Thromb Haemost 1998; 79: 859–64. The antithrombotic effects of these peptide and nonpeptide Factor Xa inhibitors have been well demonstrated in various experimental models of arterial and venous thrombosis (Kaiser B. Thrombin and factor Xa inhibitors. Drugs of the Future 23: 423–436, 1998).

SUMMARY OF THE INVENTION

One object of the present invention is to provide a method of treating thrombosis in a mammal comprising: administering to said mammal a therapeutically effective amount of a combination of (i) a Factor Xa inhibitor, and (ii) a compound selected from the group consisting of aspirin, TPA a GPIIb/IIIa antagonist, low molecular weight heparin and heparin, wherein the dose administered for at least one of (i) and (ii) is a subtherapeutic dose.

Another object of the present invention is to provide a method of treating thrombosis in a mammal wherein the combination of (i) and (ii) above are administered in amounts to provide a synergistic effect.

These and other objects, which will become apparent during the following detailed description, have been achieved by the discovery that the administration of a Factor Xa inhibitor (i) in combination with one of (ii) aspirin, tissue plasminogen activator (TPA), a GPIIb/IIIa antagonist, low molecular weight heparin or heparin, with at least one of (i) and (ii), preferably both, being administered at a dose which would be a subtherapeutic dose when administered alone.

DETAILED DESCRIPTION OF THE INVENTION

Figure 1:
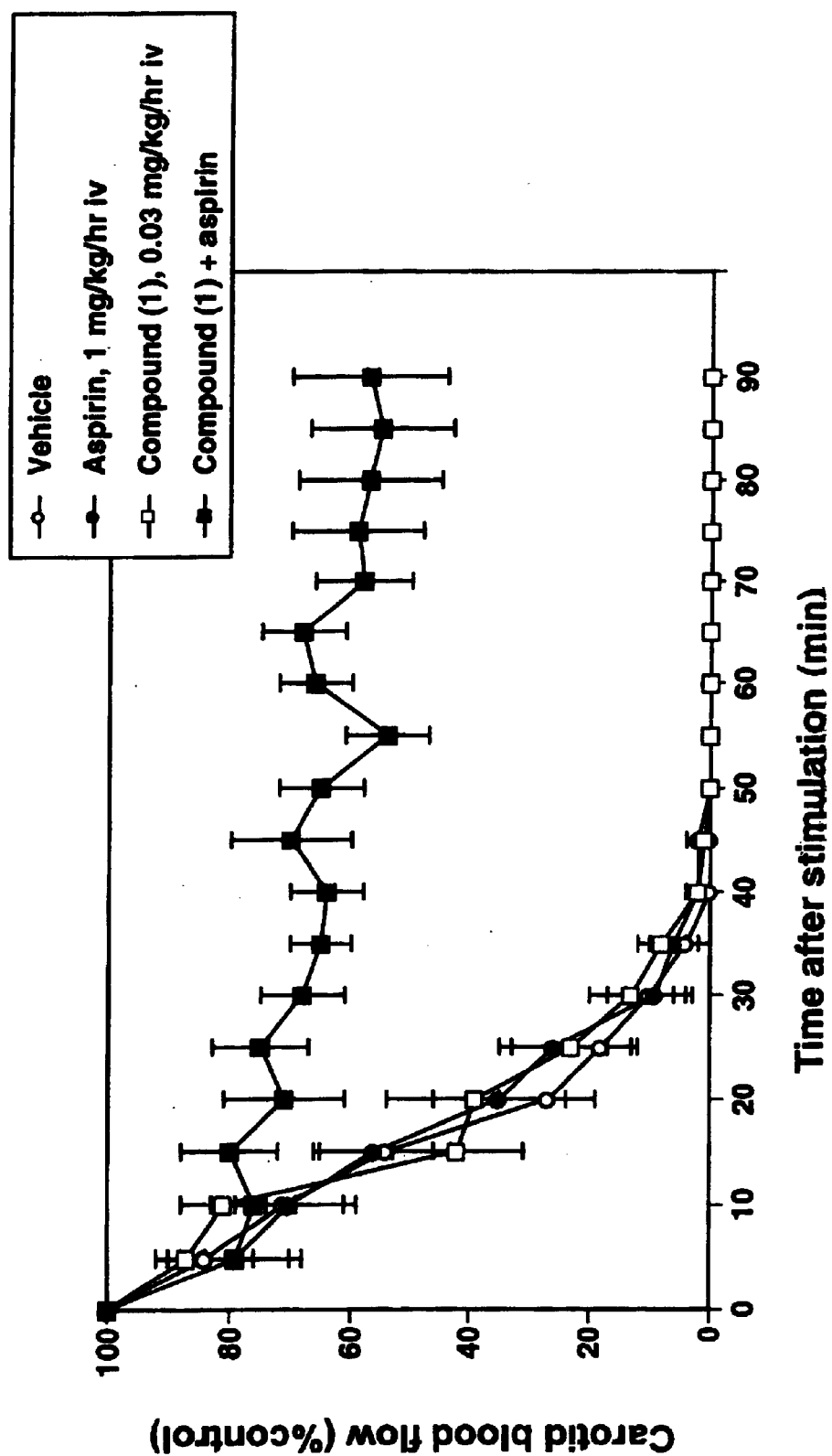
FIG. 1 is a graph showing carotid blood flow versus time for saline vehicle, aspirin alone, a Factor Xa inhibitor alone, and a combination of aspirin and the same Factor Xa inhibitor.

The combinations of active compounds (i) and (ii) of this invention are useful in the treatment of thrombotic disorders including atherosclerotic arterial disease, valvular heart disease, heart failure, cerebrovascular disease such as stroke, atrial fibrillation, coronary artery disease such as myocardial infarction and unstable angina, coronary artery bypass grafts, peripheral vascular disease, thromboembolic complications of prosthetic cardiovascular devices such heart valves and vascular grafts and deep vein thrombosis following major orthopaedic surgery, major fractures and/or abdominal surgery. These combinations are also expected to be useful in combining with endovascular stenting procedures such as percutaneous transluminal coronary angioplasty to prevent subsequent arterial thrombus formation and reocclusion.

Factor Xa inhibitor compounds (i) useful in the present invention are well-known in the prior art. Preferred Factor Xa inhibitors are described in PCT Pat. Appln. No. US97/22895, filed Dec. 15, 1997; published Jul. 2, 1998, as WO98/28269, the disclosure of which is hereby incorporated by reference. Specifically preferred compounds within WO98/28269 are:

Compound (1):

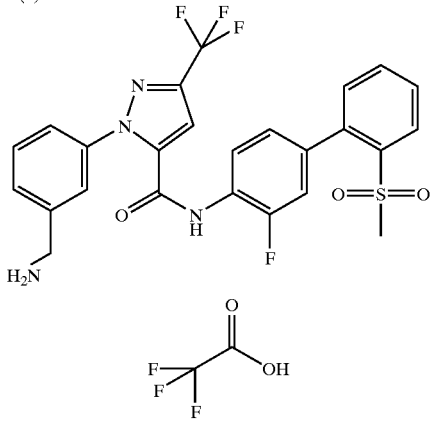

Compound (2):

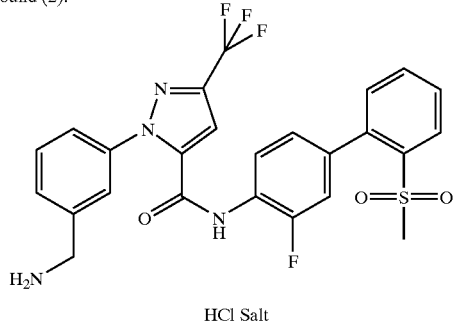

HCl Salt

Compound (3):

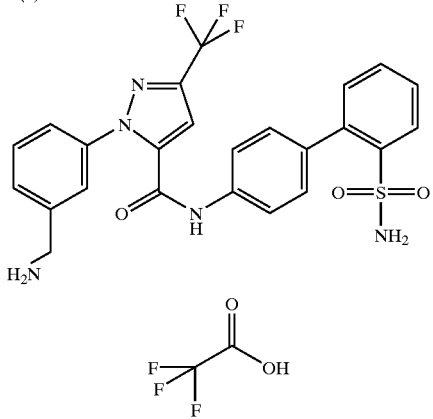

Another Factor Xa inhibitor compound is DX-9065a described in Thromb Haemost 1994; 71:314–9; and Thromb Haemost 1994; 72:393–6. DX-9065a is (+)-2S-2[4-[[(3S)-1-acetimidoyl-3-pyrrolidinyl]oxy]phenyl]-3-[7-amidino-2-naphthyl] propanoic acid hydrochloride pentahydrate. A still further Factor Xa inhibitor compound is YM-60828 described in Thromb Haemost 1998; 79:859–64. YM-60828 is [N-[4-[(1-acetimidoyl-4-piperidyl)oxy]phenyl]-N-[(7-amidino-2-naphthyl)methyl]sulfamoyl]acetic acid dihydrochloride. Other Factor Xa inhibitor compounds will be readily known by those skilled in the art.

The compounds (ii) useful in the combination of the present invention are either commercially available and/or well-known in the prior art. Aspirin, fragmin (Pharmacia AB, Stockholm, Sweden), heparin (Upjohn, Kalamazoo, Mich.), and TPA (Genentech, San Francisco, Calif.) are available commercially. Fragmin is a low molecular weight heparin. It is isolated from standard heparin with a mean molecular weight of 4.5 kDa whereas standard heparin has a molecular weight of 750 to 1000 kDa. Low-molecular-weight heparin such as fragmin differs from heparin in both their pharmacokinetic properties and mechanism of action. The potency for fragmin is expressed in unit of anti-Factor Xa activity. Each mg of fragmin has about 150 U of anti-Factor Xa activity.

Preferred GPIIb/IIIa antagonist compounds useful as component (ii) of the combination are described in published PCT Application WO95/14683, published 1 Jun. 1995, as the second embodiment. Preferred compounds described therein have the formula:

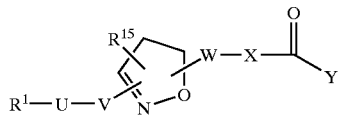

(Ia)

or a pharmaceutically acceptable salt thereof, wherein:

R1 is selected from R2a(R3)N—, R2(R3)N(R2N=)C—, R2a(R3)N(CH2)p'Z—, R2(R3)N(R2N=)C(CH2)p"Z—, R2(R3)N(R2N=)CN(R2)—, R2(R3)NC(O)—, R2(R5O)N(R2N=)C—, R2(R3)N(R5ON=)C—;

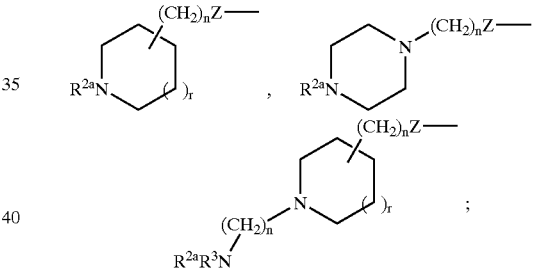

Z is selected from a bond, O, or S;

R2 and R3 are independently selected from: H; C1–C6 alkyl; C7–C11 arylalkyl optionally substituted with 0–3 groups selected from hydroxy, halogen, C1–C6 alkoxy, C1–C6 alkyl, CF3, S(O)mCH3, —N(CH3)2, C1–C4 haloalkyl, methylenedioxydiyl, ethylenedioxydiyl; (C1–C10 alkoxy)carbonyl; aryl(C1–C10 alkoxy)carbonyl where the aryl group is optionally substituted with 0–3 groups selected from hydroxy, halogen, C1–C6 alkoxy, C1–C6 alkyl, CF3, S(O)mCH3, —N(CH3)2, C1–C4 haloalkyl, methylenedioxydiyl, ethylenedioxydiyl; or heteroaryl(C1–C5)alkyl where the heteroaryl group is optionally substituted with 0–2 groups selected from hydroxy, halogen, C1–C6 alkoxy, C1–C6 alkyl, CF3, S(O)mCH3, —N(CH3)2, C1–C4 haloalkyl, methylenedioxydiyl, ethylenedioxydiyl;

R2a is R2 or R2(R3)N(R2N=)C;

U is a single bond,

V is selected from:

a single bond;

—(C$_1$–C$_7$ alkyl)-, substituted with 0–3 groups independently selected from R$^6$ or R$^7$;

—(C$_2$–C$_7$ alkenyl)-, substituted with 0–3 groups independently selected from R$^6$ or R$^7$;

—($C_2$–$C_7$ alkynyl)-, substituted with 0–3 groups independently selected from $R^6$ or $R^7$;

-(phenyl)-Q—, said phenyl substituted with 0–2 groups independently selected from $R^6$ or $R^7$;

-(pyridyl)-Q—, said pyridyl substituted with 0–2 groups independently selected from $R^6$ or $R^7$; or -(pyridazinyl)-Q—, said pyridazinyl substituted with 0–2 groups independently selected from $R^6$ or $R^7$, Q is selected from a single bond, —O—, —S(O)$_m$—, —N($R^{12}$)—, —(CH$_2$)m-, —C(=O)—, —N($R^{5a}$)C(=O)—, —C(=O)N($R^{5a}$)—, —CH$_2$O—, —OCH$_2$—, —CH$_2$N($R^{12}$)—, —N($R^{12}$)CH$_2$—, —CH$_2$C(=O)—, —C(=O)CH$_2$—, —CH$_2$S(O)$_m$—, or —S(O)$_m$CH$_2$—, provided that when b is a single bond, and $R^1$—U—V— is a substituent on C5 of the central 5-membered ring of Formula Ic, then Q is not —O—, —S(O)$_m$—, —N($R^{12}$)—, —C(=O)N($R^{5a}$)—, —CH$_2$O—, —CH$_2$N($R^{12}$)— or —CH$_2$S(O)$_m$—;

W is selected from:

—(C($R^4$)$_2$)—C(=O)—N($R^{5a}$)—, or

—C(=O)—N($R^{5a}$)—(C($R^4$)$_2$)—;

X is —C($R^4$)($R^8$)—CHR$^{4a}$—;

$R^4$ is selected from H, $C_1$–$C_{10}$ alkyl, $C_1$–$C_{10}$ alkylcarbonyl, aryl, arylalkyl, cycloalkyl, or cycloalkylalkyl;

$R^{4a}$ is selected from hydroxy, $C_1$–$C_{10}$ alkoxy, nitro, —N($R^5$)$R^{5a}$, —N($R^{12}$)$R^{13}$, or —N($R^{16}$)$R^{17}$, aryl substituted with 0–3 $R^6$, or ($C_1$–$C_{10}$ alkyl)carbonyl;

$R^{4b}$ is selected from H, $C_1$–$C_6$ alkyl, $C_2$–$C_6$ alkenyl, $C_2$–$C_6$ alkynyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, ($C_1$–$C_6$ alkyl)carbonyl, $C_6$–$C_{10}$ aryl, —N($R^{12}$)$R^{13}$, halo, $CF_3$, CN, ($C_1$–$C_6$ alkoxy)carbonyl, carboxy, piperidinyl, morpholinyl or pyridyl;

$R^5$ is selected from H or $C_1$–$C_{10}$ alkyl substituted with 0–6 $R^{4b}$;

$R^{5a}$ is selected from hydrogen, hydroxy, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_1$–$C_6$ alkoxy, benzyloxy, $C_6$ to $C_{10}$ aryl, heteroaryl, heteroarylalkyl, $C_7$ to $C_{11}$ arylalkyl, or adamantylmethyl, $C_1$–$C_{10}$ alkyl substituted with 0–2 $R^{4b}$;

alternately, $R^5$ and $R^{5a}$ can be taken together to be 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl, each being optionally substituted with $C_1$–$C_6$ alkyl, $C_6$–$C_{10}$ aryl, heteroaryl, $C_7$–$C_{11}$ arylalkyl, ($C_1$–$C_6$ alkyl)carbonyl, ($C_3$–$C_7$ cycloalkyl)carbonyl, ($C_1$–$C_6$ alkoxy)carbonyl or ($C_7$–$C_{11}$ arylalkoxy)carbonyl;

$R^{5b}$ is selected from $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$;

Y is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, or $C_{10}$ to $C_{14}$ (5-aryl-1,3-dioxa-cyclopenten-2-one-yl)methyloxy;

$R^6$ and $R^7$ are each independently selected from H, $C_1$–$C_{10}$ alkyl, hydroxy, $C_1$–$C_{10}$ alkoxy, nitro, ($C_1$–$C_{10}$ alkyl)carbonyl, —N($R^{12}$)$R^{13}$, cyano, or halo;

$R^{12}$ and $R^{13}$ are each independently selected from H, $C_1$–$C_{10}$ alkyl, ($C_1$–$C_{10}$ alkoxy)carbonyl, ($C_1$–$C_{10}$ alkyl)carbonyl, $C_1$–$C_{10}$ alkylsulfonyl, aryl($C_1$–$C_{10}$ alkyl)sulfonyl, arylsulfonyl, heteroarylsulfonyl, heteroarylcarbonyl, heteroarylalkylcarbonyl or aryl, wherein said aryl groups being optionally substituted with 0–3 substituents selected from the group consisting of: $C_1$–$C_4$ alkyl, $C_1$–$C_4$ alkoxy, halo, $CF_3$, and $NO_2$;

$R^{15}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or ($C_1$–$C_{10}$ alkoxy)carbonyl, $CO_2R^5$ or —C(=O)N($R^5$)$R^{5a}$;

$R^{16}$ is selected from:

—C(=O)—O—$R^{18a}$,

—C(=O)—$R^{18b}$,

—C(=O)N($R^{18b}$)$_2$,

—SO$_2$—$R^{18a}$, or

—SO$_2$—N($R^{18b}$)$_2$;

$R^{17}$ is selected from: H or $C_1$–$C_5$ alkyl;

$R^{18a}$ is selected from:

$C_1$–$C_8$ alkyl substituted with 0–2 $R^{19}$, $C_2$–$C_8$ alkenyl substituted with 0–2 $R^{19}$, $C_2$–$C_8$ alkynyl substituted with 0–2 $R^{19}$, $C_3$–$C_8$ cycloalkyl substituted with 0–2 $R^{19}$, aryl substituted with 0–4 $R^{19}$, aryl($C_1$–$C_6$ alkyl)- substituted with 0–4 $R^{19}$, a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, piperidinyl, indolinyl, or morpholinyl, said heterocyclic ring being substituted with 0–4 $R^{19}$;

$C_1$–$C_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, pyrrolidinyl, piperidinyl, indolinyl, or morpholinyl, said heterocyclic ring being substituted with 0–4 $R^{19}$;

$R^{18b}$ is selected from $R^{18a}$ or H;

$R^{19}$ is selected from H, halogen, $CF_3$, CN, $NO_2$, $NR^{12}R^{13}$, $C_1$–$C_8$ alkyl, $C_2$–$C_6$ alkenyl, $C_2$–$C_6$ alkynyl, $C_1$–$C_6$ alkoxy, $C_3$–$C_{11}$ cycloalkyl, $C_4$–$C_{11}$ cycloalkylalkyl, aryl, heteroaryl, aryl($C_1$–$C_6$ alkyl)-, ($C_1$–$C_4$ alkyl)sulfonyl, aryl-sulfonyl, or $C_1$–$C_4$ alkoxycarbonyl;

n is 0–4;

p' is 1–7;

p" is 1–7;

r is 0–3.

More preferred compounds have the formula:

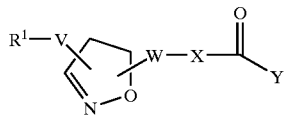

(1b)

or a pharmaceutically acceptable salt thereof, wherein:
R$^1$ is selected from: R$^{2a}$(R$^3$)N—, R$^2$NH(R$^2$N=)C—, R$^2$NH(R$^2$N=)CNH—, R$^{2a}$(R$^3$)N(CH$_2$)$_{p'}$Z—, R$^2$NH(R$^2$N=)C(CH$_2$)$_{p''}$Z—, R$^2$(R$^3$)NC(O)—, R$^2$(R$^5$O)N(R$^2$N=)C—, R$^2$(R$^3$)N(R$^5$ON=)C—;

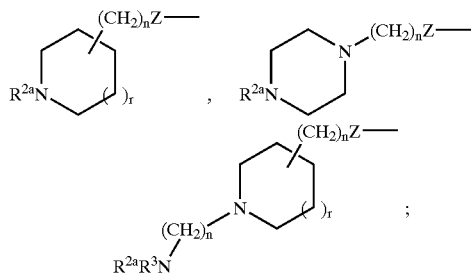

n is 0–1;
p' is 4–6;
p" is 2–4;
Z is selected from a bond or O;
V is a single bond, -(phenyl)- or -(pyridyl)-;
W is selected from:
 —(C(R$^4$)$_2$)—C(=O)—N(R$^{5a}$)—,
 —C(=O)—N(R$^{5a}$)—CH$_2$—;
X is selected from:
 —CH$_2$—CH(N(R$^{16}$)R$^{17}$)—, or
 —CH$_2$—CH(NR$^5$R$^{5a}$)—;
Y is selected from:
 hydroxy;
 C$_1$ to C$_{10}$ alkoxy;
 methylcarbonyloxymethoxy-;
 ethylcarbonyloxymethoxy-;
 t-butylcarbonyloxymethoxy-;
 cyclohexylcarbonyloxymethoxy-;
 1-(methylcarbonyloxy)ethoxy-;
 1-(ethylcarbonyloxy)ethoxy-;
 1-(t-butylcarbonyloxy)ethoxy-;
 1-(cyclohexylcarbonyloxy)ethoxy-;
 i-propyloxycarbonyloxymethoxy-;
 t-butyloxycarbonyloxymethoxy-;
 1-(i-propyloxycarbonyloxy)ethoxy-;
 1-(cyclohexyloxycarbonyloxy)ethoxy-;
 1-(t-butyloxycarbonyloxy)ethoxy-;
 dimethylaminoethoxy-;
 diethylaminoethoxy-;
 (5-methyl-1,3-dioxacyclopenten-2-on-4-yl)methoxy-;
 (5-(t-butyl)-1,3-dioxacyclopenten-2-on-4-yl)methoxy-;
 (1,3-dioxa-5-phenyl-cyclopenten-2-on-4-yl)methoxy-;
 1-(2-(2-methoxypropyl)carbonyloxy)ethoxy-;
R$^{16}$ is selected from:
 —C(=O)—O—R$^{18a}$,
 —C(=O)—R$^{18b}$,
 —S(=O)$_2$—R$^{18a}$ or
 —SO$_2$—N(R$^{18b}$)$_2$;
R$^{17}$ is selected from H or C$_1$–C$_5$ alkyl;
R$^{18a}$ is selected from:
 C$_1$–C$_8$ alkyl substituted with 0–2 R$^{19}$,
 C$_2$–C$_8$ alkenyl substituted with 0–2 R$^{19}$,
 C$_2$–C$_8$ alkynyl substituted with 0–2 R$^{19}$,
 C$_3$–C$_8$ cycloalkyl substituted with 0–2 R$^{19}$,
 aryl substituted with 0–4 R$^{19}$,
 aryl(C$_1$–C$_6$ alkyl)- substituted with 0–4 R$^{19}$,
 a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, piperidinyl, indolinyl, or morpholinyl, said heterocyclic ring being substituted with 0–4 R$^{19}$;
 C$_1$–C$_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, pyrrolidinyl, piperidinyl, indolinyl, or morpholinyl, said heterocyclic ring being substituted with 0–4 R$^{19}$.

A specifically preferred compound has the formula:

Compound (4):

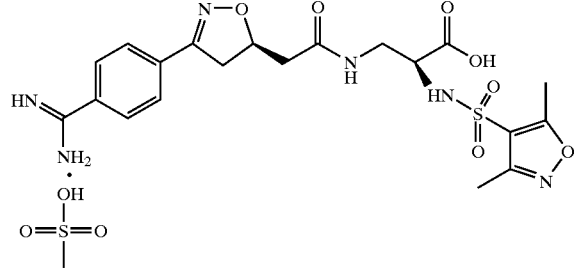

Other salts of this compound are also specifically preferred.

Specific examples of other GPIIb/IIIa antagonist compounds are abciximab, eptifibatide, tirofiban, lamifiban, lefradafiban, sibrafiban (Ro-48-3657), orbofiban and xemilofiban described in the paper of Graul et al. and Scarborough (Graul A, Martel A M and Castaner J. Xemilofiban; Drugs of the Future 22: 508–517, 1997; Scarborough R M; Eptifibatide. Drugs of the Future 23: 585–590, 1998). Others will be readily apparent to those skilled in the art.

"Therapeutically effective amount" is intended to include an amount of a combination of compounds claimed effective to treat thrombosis in a mammal. The combination of compounds is preferably a synergistic combination. Synergy, as described for example by Chou and Talalay, Adv. Enzyme Regul. 22:27–55 (1984), occurs when the effect (in this case, an antithrombotic effect) of the compounds when administered in combination is greater than the additive effect of the compounds when administered alone as a single agent. In general, a synergistic effect is most clearly demonstrated at suboptimal concentrations of the compounds. Synergy can be in terms of antihypertensive effect, antithrombotic effect, or some other non-additive beneficial effect of the combination compared with the individual components.

By "administered in combination", "combination", or "combined" when referring to component (i) and component (ii) of the present invention, it is meant that the components are administered concurrently to the mammal being treated. When administered in combination each component may be administered at the same time or sequentially in any order or at different points in time. Thus, component (i) and component (ii) may be administered separately but sufficiently closely in time so as to provide the desired therapeutic effect.

By "subtherapeutic dose" when referring to component (i) and component (ii) of the present invention, it is meant that each component when administered to a mammal alone does not give the desired therapeutic effect for the disease being treated.

The invention can be understood further by the following examples wherein Compounds (1)–(4) are as shown above. Saline (0.9 weight % NaCl) is the vehicle in all examples.

EXAMPLE 1

The Combination of Aspirin and a Factor Xa Inhibitor

Rabbits were anesthetized with ketamine (50 mg/kg i.m.) and xylazine (10 mg/kg i.m.) and then surgically prepared with arterial and venous catheters. An electromagnetic flow probe was placed on a segment of an isolated carotid artery to monitor blood flow. Thrombus formation was induced by electrical stimulation of the carotid artery for 3 min at 4 mA using an external stainless-steel bipolar electrode. Carotid blood flow was measured continuously over a 90-min period to monitor thrombus occlusion. Test agents were infused intravenously 1 hour prior to the electrical stimulation of the carotid artery and continuously during the 90-min period.

As shown in FIG. 1 following the electrical stimulation, thrombus formation was induced and carotid blood flow was gradually declined in saline vehicle-treated animals. At about 40 min after stimulation, the artery was totally occluded and blood flow was zero. Aspirin at 1 mg/kg/hr i.v. (concentration in saline was 0.167 mg/ml) or Compound (1) (a Factor Xa inhibitor) at 0.1 mg/kg/hr i.v. (concentration in saline was 0.017 mg/ml) did not prevent the occlusion of the artery; and blood flow in these animals was decreased to zero at about the same time as those in vehicle-treated animals. Surprisingly, Compound (1) 0.1 mg/kg/hr i.v. in combination with aspirin at 1 mg/kg/hr i.v. prevented the artery from occlusion and maintained the blood flow for at least 90 min. These results indicate that a combination of Compound (1) and aspirin at their subtherapeutic doses unexpectedly produced a significant antithrombotic effect in a rabbit model of arterial thrombosis.

EXAMPLE 2

Figure 2:
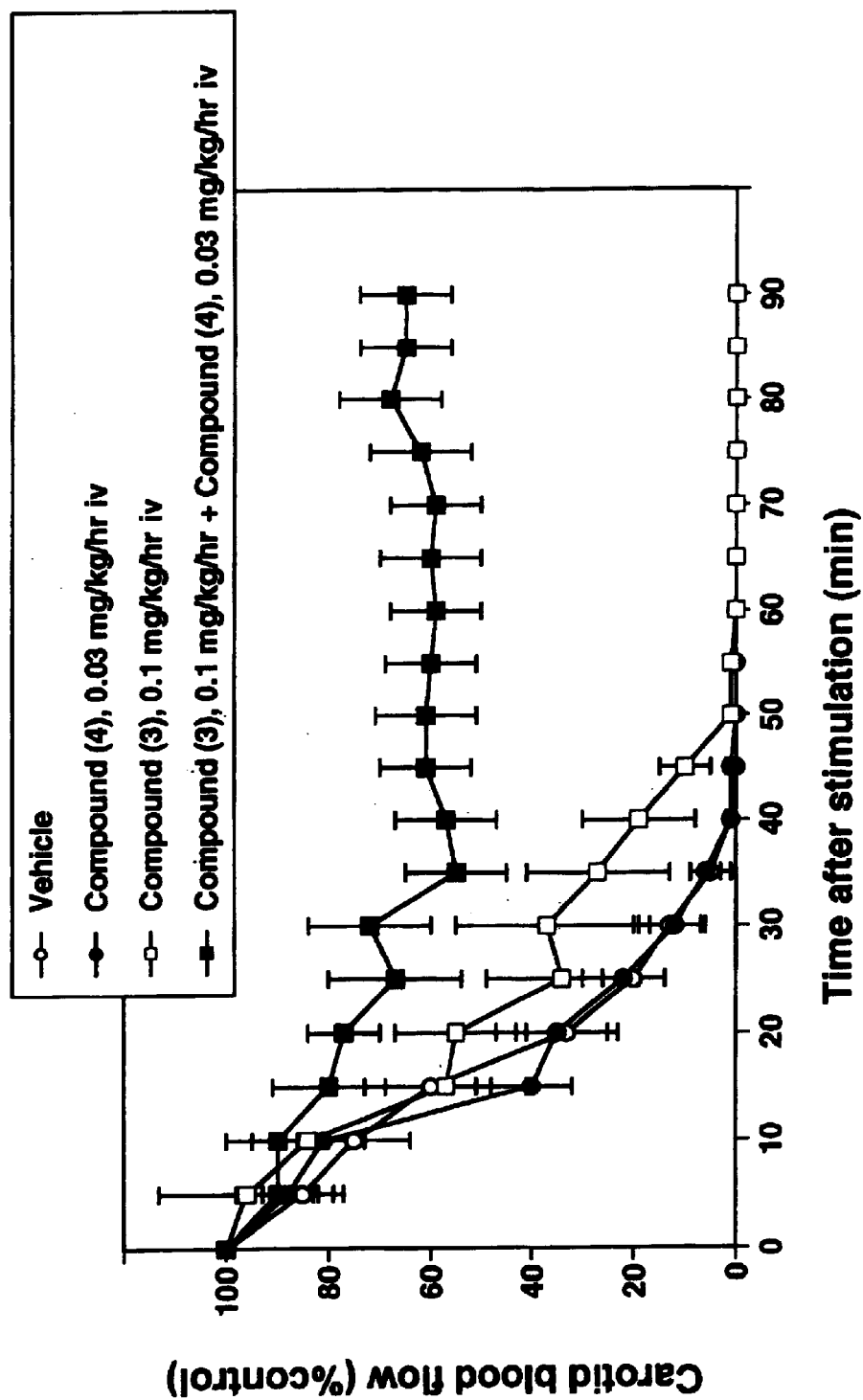
FIG. 2 is a graph showing carotid blood flow versus time for saline vehicle, a GPIIb/IIIa antagonist alone, a Factor Xa inhibitor alone, and a combination of the same IIb/IIIa antagonist and Factor X inhibitor.

The Combination of Compound (4) (a GP-IIb/IIIa Antagonist) and a Factor Xa Inhibitor Experimental protocol was described as above for Example 1. As shown in FIG. 2, Compound (4) (a GP-IIb/IIIa antagonist) at 0.03 mg/kg/hr i.v. and Compound (3) (a Factor Xa inhibitor) at 0.1 mg/kg/hr i.v. did not prevent the occlusion of the artery; and blood flow in these animals was decreased to zero at about the same time as those in vehicle-treated animals. Surprisingly, Compound (3) at 0.1 mg/kg/hr i.v. (concentration in saline was 0.017 mg/ml) in combination with Compound (4) at 0.03 mg/kg/hr i.v. (concentration in saline was 0.005 mg/ml) prevented the artery from occlusion and maintained the blood flow for at least 90 min. These results indicate that a combination of Compound (3) and Compound (4) at their subtherapeutic doses unexpectedly produced a significant antithrombotic effect in a rabbit model of arterial thrombosis.

EXAMPLE 3

Figure 3:
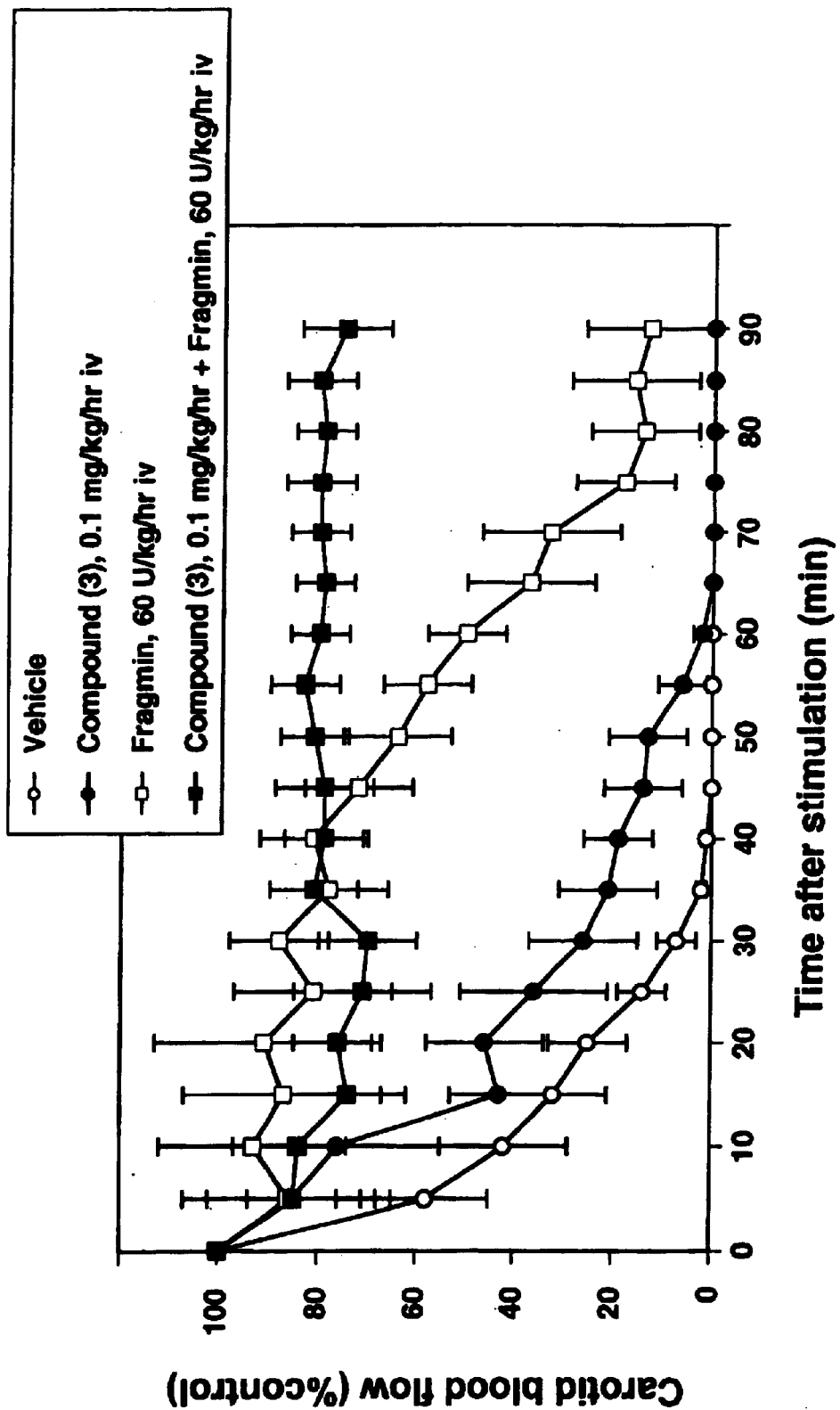
FIG. 3 is a graph showing carotid blood flow versus time for saline vehicle, fragmin, a Factor Xa inhibitor, and a combination of fragmin and the same Factor Xa inhibitor.

The Combination of Fragmin (Low-molecular-weight-heparin) and a Factor Xa Inhibitor Experimental protocol was described as above for Example 1. As shown in FIG. 3, fragmin (a low-molecular-weight-heparin) at 60 U/kg/hr i.v. was moderately active. Compound (3) (a Factor Xa inhibitor) at 0.1 mg/kg/hr i.v. did not prevent the occlusion of the artery; and blood flow in these animals was decreased to zero similar to those in vehicle-treated animals. Surprisingly, Compound (3) at 0.1 mg/kg/hr i.v. (concentration in saline was 0.017 mg/ml) in combination with fragmin at 60 U/kg/hr i.v. (concentration in saline was 0.067 mg/ml or 10 U/ml) prevented the artery from occlusion and maintained the blood flow for at least 90 min. These results indicate that a combination of Compound (3) at its subtherapeutic dose and fragmin at a medium dose unexpectedly produced a significant antithrombotic effect in a rabbit model of arterial thrombosis.

EXAMPLE 4

Figure 4:
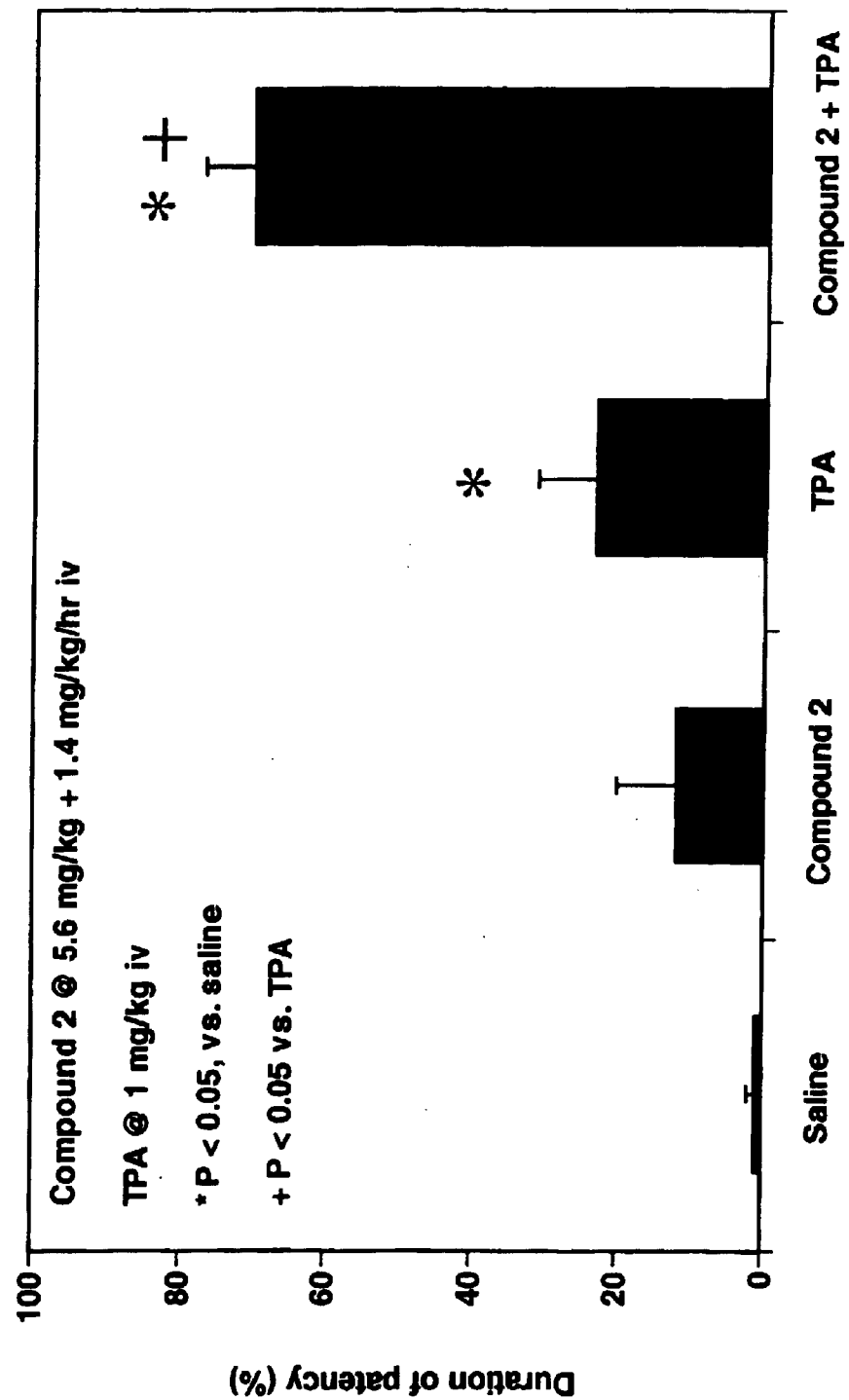
FIG. 4 is a bar chart showing the duration of patency for saline vehicle, a Factor Xa inhibitor alone, TPA alone, and a combination of the same TPA and Factor Xa inhibitor.

The Combination of Recombinant Tissue-type Plasminogen Activator (TPA) and a Factor Xa Inhibitor Experiments were conducted in rats. It is similar to that of the rabbit protocol as described above in Example 1 except that Compound (2) and/or TPA were given 5 min after a preformed clot was formed. The measured parameter is its duration of patency. As shown in FIG. 4, five minutes after the induction of occlusive thrombosis, neither Compound (2) at 5.6 mg/kg (concentration in saline was 0.23 mg/ml) and 1.4 mg/kg/hr i.v. nor TPA at 1 mg/kg i.v. (concentration in saline was 1 mg/ml) produced a therapeutic effect on the duration of patency. However, a combination of Compound (2) at 5.6 mg/kg and 1.4 mg/kg/hr i.v., and TPA at 1 mg/kg i.v. increased the duration of patency to 70%. This result suggests that a Factor Xa inhibitor such as Compound (2) is a promising useful adjunctive agent, which accelerates thrombolysis induced by TPA or other thrombolytic agents. Compound a (2) enhanced the thrombolysis induced by a subtherapeutic dose of TPA.

EXAMPLE 5

The Combination of Heparin and a Factor Xa Inhibitor

Figure 5:
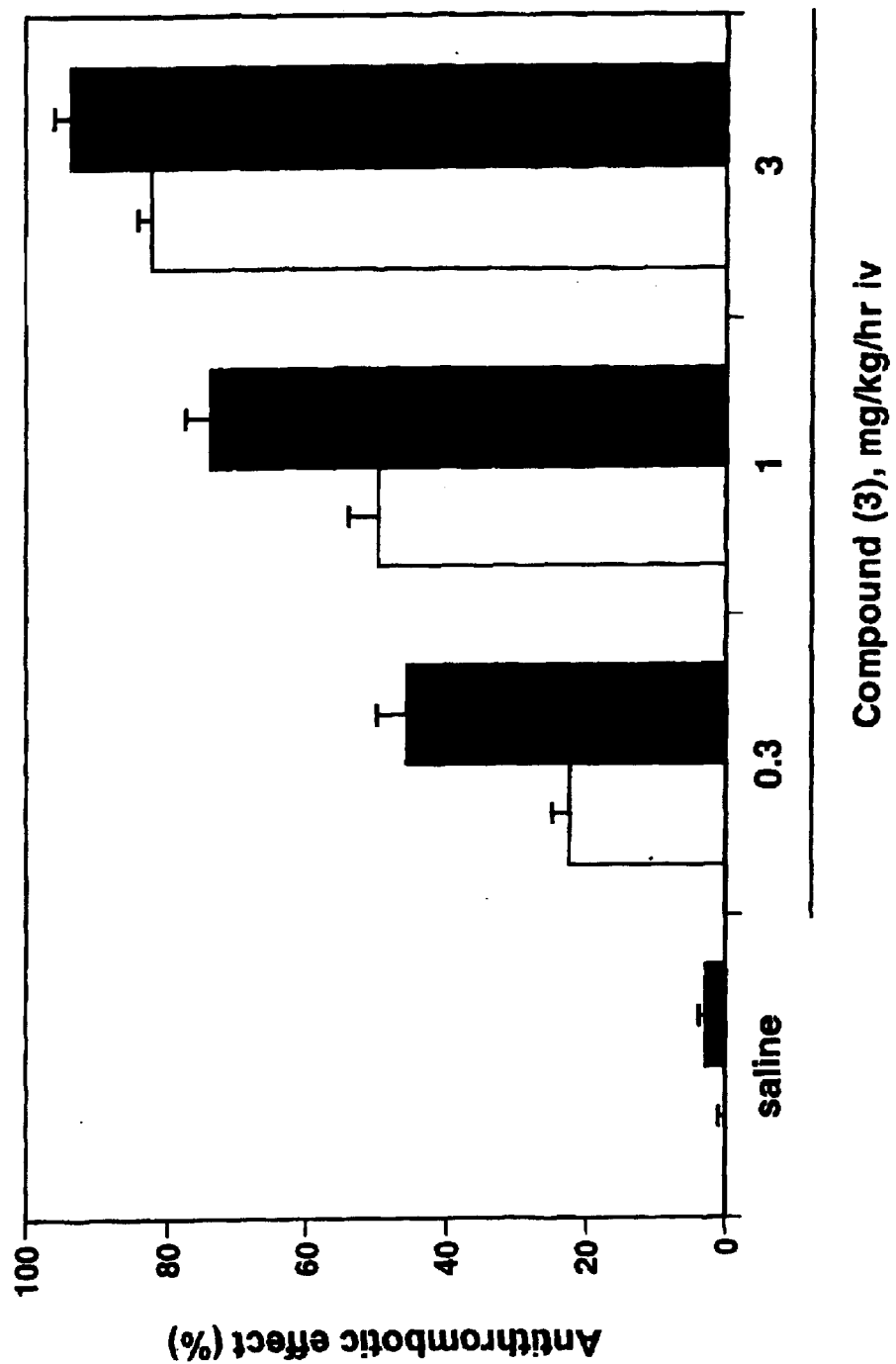
FIG. 5 is a bar chart showing the antithrombotic effect of a saline vehicle and heparin alone, and a combination of heparin with 3 different doses of a Factor Xa inhibitor.

Experiments were conducted in male guinea pigs anesthetized with a mixture of ketamine (90 mg/kg i.m.) and xylazine (12 mg/kg i.m.). The arterio-venous shunt was connected between the carotid artery and jugular vein. The exposure of flowing blood to a silk thread induced the formation of a significant thrombus. Thirty minutes later, the shunt was disconnected and the silk thread covered with thrombus was weighed. The compounds or saline vehicle were given as continuous i.v. infusion starting 1 hr before blood was circulated in the shunt and continuing throughout the experiment (i.e., 90 min). As shown in FIG. 5, heparin at 4 U/kg/hr i.v. (concentration in saline was 0.667 U/ml) did not cause antithrombotic effect. However, heparin at 4 U/kg/hr i.v. potentiated the antithrombotic effects of Compound (3) (a Factor Xa inhibitor) at 0.3, 1 or 3 mg/kg/hr i.v. (concentration in saline for 0.3 dose was 0.05 mg/ml). This result suggests that heparin at a subtherapeutic dose enhances the antithrombotic effect of Compound (3) in a guinea model of venous thrombosis.

The results presented indicate that a combination therapy comprising a Factor Xa inhibitor and one of aspirin, TPA, a GPIIb/IIIa antagonist, low molecular weight heparin or heparin will be effective in treating thrombosis in patients. The method of the present invention provides important advantages over currently available treatments for thrombosis.

Dosage and Formulation

The Factor Xa inhibitor (i) and a compound (ii) of this invention can be administered as treatment for thrombosis by any means that produces contact of the active agent with the agents site of action, i.e., Factor Xa, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.01 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in Remington's Pharmaceutical Sciences, 17th ed., Mack Publishing Company, Easton, Pa., 1985, a standard reference text in this field, the disclosure of which is hereby incorporated by reference.

Useful pharmaceutical dosage-forms for administration of the compounds of this invention can be illustrated as follows:

Capsules

A large number of unit capsules can be prepared by filling standard two-piece hard gelatin capsules each with 0.1 to 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 0.1 to 100 mg of the active ingredient. The capsules should then be washed and dried.

Tablets

A large number of tablets can be prepared by conventional procedures so that the dosage unit is 0.1 to 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 0.1 to 100 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 0.1 to 100 mg by weight of active ingredient in 10% by volume propylene glycol and water. The solution is sterilized by commonly used techniques.

Combination of Components (i) and (ii)

Each therapeutic agent component of this invention can independently be in any dosage form, such as those described above, and can also be administered in various ways, as described above. In the following description component (ii) is to be understood to represent one or more agents as described previously. Thus, if components (i) and (ii) are to be treated the same or independently, each agent of component (ii) may also be treated the same or independently.

Components (i) and (ii) of the present invention may be formulated together, in a single dosage unit (that is, combined together in one capsule, tablet, powder, or liquid, etc.) as a combination product. When component (i) and (ii) are not formulated together in a single dosage unit, the component (i) may be administered at the same time as component (ii) or in any order; for example component (i) of this invention may be administered first, followed by administration of component (ii), or they may be administered in the reverse order. If component (ii) contains more that one agent, e.g., aspirin and heparin, these agents may be administered together or in any order. When not administered at the same time, preferably the administration of component (i) and (ii) occurs less than about one hour apart. Preferably, the route of administration of component (i) and (ii) is intravenously (i.v.). The terms oral agent, oral inhibitor, oral compound, or the like, as used herein, denote compounds which may be orally administered. Although it is preferable that component (i) and component (ii) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (i) and (ii) of the present invention will be readily ascertainable by a medical practitioner skilled in the art, based upon the present disclosure. By way of general guidance, typically a daily dosage may be about 0.01 milligram to about 1 gram of each component. If component (ii) represents more than one compound, then typically a daily dosage may be about 0.01 milligram to about 0.1 gram of each agent of component (ii). By way of general guidance, when the compounds of component (i) and component (ii) are administered in combination, the dosage amount of each component may be reduced by about 70–80% relative to the usual dosage of the component when it is administered alone as a single agent for the treatment of thrombosis, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose or other appropriate materials as known in the art, in order to further separate the active components. The polymer coating serves to form an additional barrier to interaction with the other component. In each formulation wherein contact is prevented between components (i) and (ii) via a coating or some other material, contact may also be prevented between the individual agents of component (ii).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Obviously, numerous modifications and variations of the present invention are possible in light of the above teachings. It is therefore to be understood that within the scope of the appended claims, the invention may be practiced otherwise than as specifically described herein.

What is claimed is:

1. A method of treating thrombosis in a mammal comprising: administering to said mammal a synergistically effective therapeutic amount of a combination of (i) a Factor Xa inhibitor, and (ii) aspirin, wherein the dose administered for at least one of (i) and (ii) is a subtherapeutic dose.

2. A method of treating thrombosis according claim 1, wherein the Factor Xa inhibitor is:

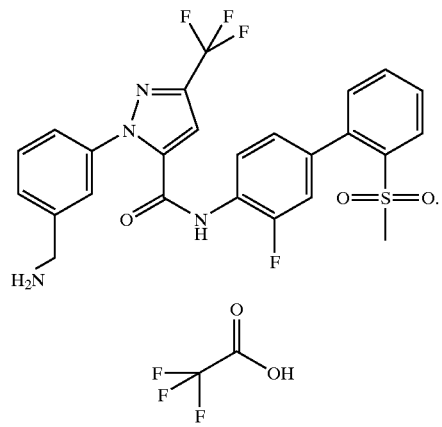

3. A method of treating thrombosis according claim 1, wherein the Factor Xa inhibitor is:

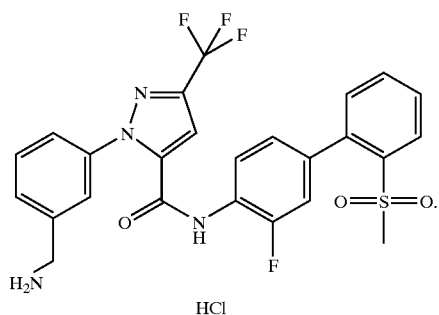

4. A method of treating thrombosis according claim 1, wherein the Factor Xa inhibitor is:

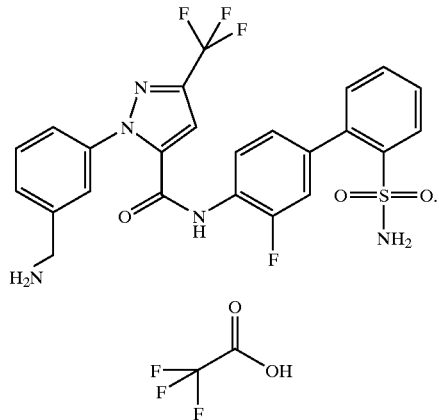

* * * * *